(12) United States Patent
Douget et al.

(10) Patent No.: US 10,070,906 B2
(45) Date of Patent: Sep. 11, 2018

(54) DEVICE AND METHOD FOR SECURING A LIGATURE TO AN OSSEOUS STRUCTURE

(71) Applicant: Zimmer Spine, Bordeaux (FR)

(72) Inventors: Stephane Douget, Quimper (FR); Richard Minfelde, Paris (FR); Gilles Larroque-Lahitette, Lagor (FR)

(73) Assignee: Zimmer Spine (FR)

( * ) Notice: Subject to any disclaimer, the term of this patent is extended or adjusted under 35 U.S.C. 154(b) by 127 days.

(21) Appl. No.: 14/750,904

(22) Filed: Jun. 25, 2015

(65) Prior Publication Data

US 2015/0366598 A1 Dec. 24, 2015

Related U.S. Application Data

(63) Continuation of application No. 13/309,995, filed on Dec. 2, 2011, now Pat. No. 9,101,425.

(30) Foreign Application Priority Data

Dec. 16, 2010 (EP) .................................... 10306428

(51) Int. Cl.
*A61B 17/70* (2006.01)
*A61B 17/82* (2006.01)
*A61B 17/84* (2006.01)

(52) U.S. Cl.
CPC .......... *A61B 17/82* (2013.01); *A61B 17/7053* (2013.01); *A61B 17/84* (2013.01); *A61B 17/842* (2013.01); *A61B 17/707* (2013.01)

(58) Field of Classification Search
CPC . A61B 17/7022; A61B 17/7053; A61B 17/82; A61B 17/823; A61B 17/842; A61B 17/84
See application file for complete search history.

(56) References Cited

U.S. PATENT DOCUMENTS 4,156,574 A 5/1979 Boden
4,769,874 A * 9/1988 Tracy ..................... A44B 99/00
24/115 G (Continued)

FOREIGN PATENT DOCUMENTS

EP 2047813 A1 4/2009
WO WO-2004019797 A2 3/2004

OTHER PUBLICATIONS

"U.S. Appl. No. 13/309,995, Advisory Action dated Jan. 23, 2015", 3 pgs.

(Continued)

*Primary Examiner* — Kevin T Truong
*Assistant Examiner* — Tracy Kamikawa
(74) *Attorney, Agent, or Firm* — Schwegman Lundberg & Woessner, P.A.

(57) ABSTRACT

Embodiments disclosed herein provide a device for securing a ligature to an osseous structure, the device comprising a first part, a second part, a flexible elongate member for engaging the osseous structure, a closure element, and a deformable element between the first and second parts for holding open a gap G between them. The flexible elongate member is threaded through an orifice in the first part and the gap G. The closure element is configured for clamping the first and second parts against each other, overcoming the resilience of the deformable element, so as to frictionally lock the flexible elongate member threaded through the gap G. Embodiments disclosed herein also provide a method for using the device.

16 Claims, 5 Drawing Sheets

(56) References Cited

U.S. PATENT DOCUMENTS

| | | | |
|---|---|---|---|
| 5,737,808 A | 4/1998 | Ikeda | |
| 7,255,701 B2* | 8/2007 | Allen | A61B 17/82 606/74 |
| 9,101,425 B2 | 8/2015 | Douget et al. | |
| 2005/0131404 A1 | 6/2005 | Mazda et al. | |
| 2007/0032825 A1* | 2/2007 | Bonutti | A61B 17/0487 606/232 |
| 2009/0248077 A1* | 10/2009 | Johns | A61B 17/7011 606/246 |

OTHER PUBLICATIONS

"U.S. Appl. No. 13/309,995, Final Office Action dated Nov. 4, 2014", 24 pgs.

"U.S. Appl. No. 13/309,995, Non-Final Office Action dated May 6, 2014", 20 pgs.

"U.S. Appl. No. 13/309,995, Notice of Allowance dated Apr. 3, 2015", 5 pgs.

"U.S. Appl. No. 13/309,995, Response filed Jan. 30, 2014 to Restriction Requirement dated Dec. 30, 2013", 6 pgs.

"U.S. Appl. No. 13/309,995, Response filed Jul. 15, 2014 to Non-Final Office Action dated May 6, 2014", 13 pgs.

"U.S. Appl. No. 13/309,995, Response filed Dec. 18, 2014 to Final Office Action dated Nov. 4, 2014", 8 pgs.

"U.S. Appl. No. 13/309,995, Restriction Requirement dated Dec. 30, 2013", 7 pgs.

"European Application Serial No. 10306428.3, Communication Pursuant to Article 94(3) EPC dated Mar. 20, 2013", 5 pgs.

"European Application Serial No. 10306428.3, Decision to grant dated Apr. 3, 2014", 2 pgs.

"European Application Serial No. 10306428.3, Extended European Search Report dated Jun. 7, 2011", 7 pgs.

"European Application Serial 10306428.3, Intention to Grant dated Dec. 17, 2013", 22 pgs.

"European Application Serial No. 10306428.3, Response filed Jul. 30, 2013 to Communication Pursuant to Article 94(3) EPC dated Mar. 20, 2013", 8 pgs.

"European Application Serial No. 10306428.3, Response filed Dec. 20, 2012 to Extended European Search Report dated Jun. 7, 2011", 8 pgs.

\* cited by examiner

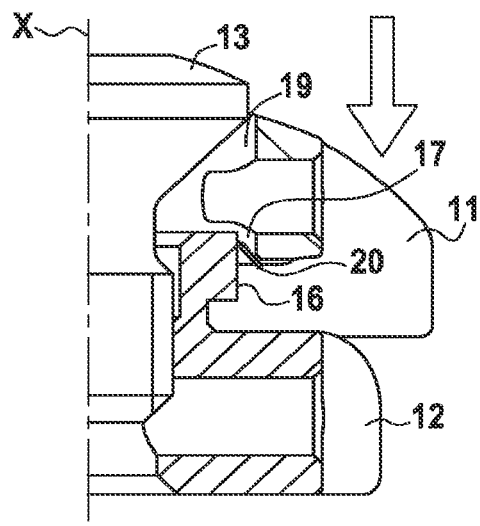 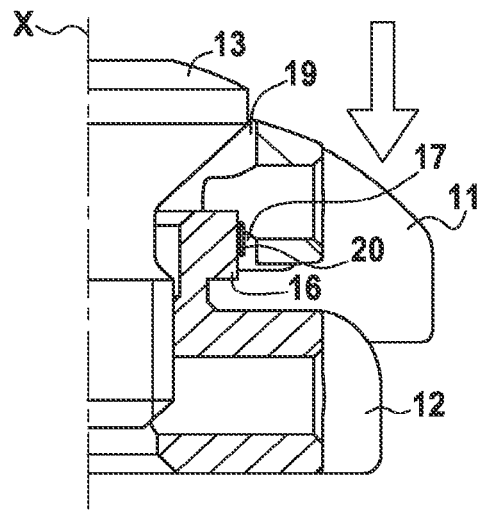
FIG.6A  FIG.6B
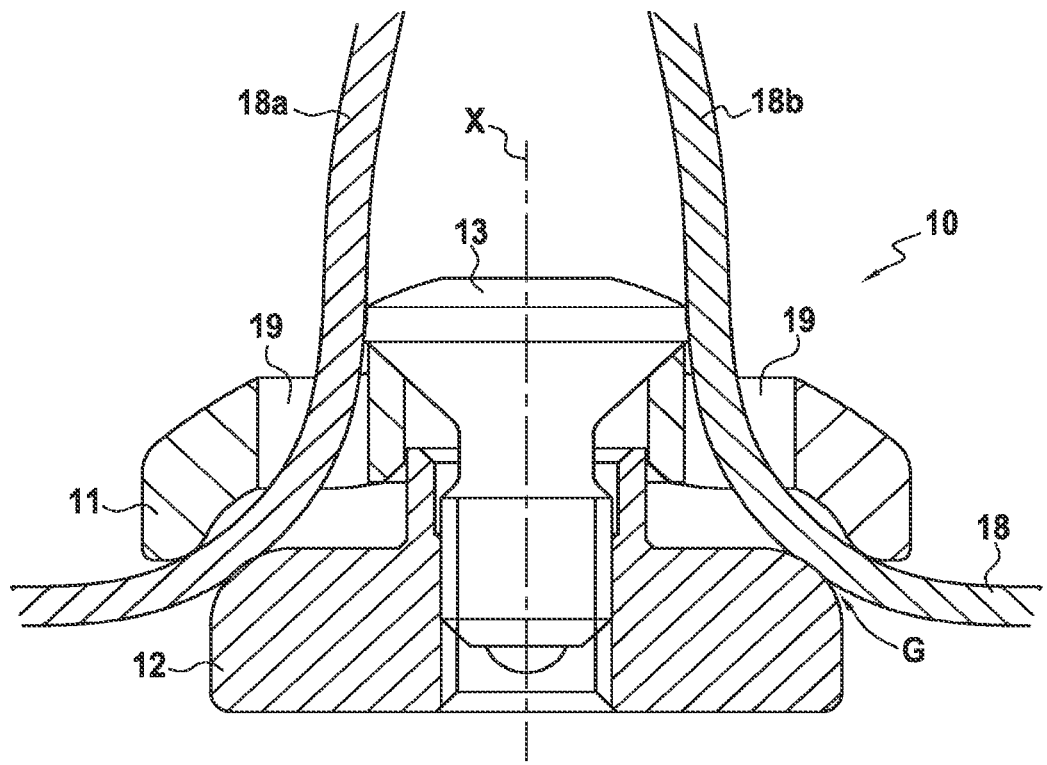
FIG.7

DEVICE AND METHOD FOR SECURING A LIGATURE TO AN OSSEOUS STRUCTURE

CROSS-REFERENCE TO RELATED APPLICATION

This application is a continuation of U.S. patent application Ser. No. 13/309,995, filed Dec. 2, 2011, now U.S. Pat. No. 9,101,425 the entirety of which are hereby incorporated into this application.

TECHNICAL FIELD

Embodiments relate to a device and a method for securing a ligature to an osseous structure, in particular for reinforcing, or stabilizing the osseous structure, or for correcting a deformity in the osseous structure.

BACKGROUND

In all vertebrate animals, including humans, osseous structures provide an essential solid framework for the body. Injury, age or disease may however damage these osseous structures. In order to repair or at least alleviate such damage, various medical and surgical techniques have been proposed. In particular, a number of surgical techniques have been proposed using wire ligatures to reinforce or correct such injured, diseased, or otherwise damaged osseous structures.

Surgical wiring techniques have in particular been applied for treatment of the spine, and more especially of upper cervical fractures and thoraco-lumbar fractures. For example, the Gallie and Brooks atlanto-axial stabilization techniques using wires can be used for the treatment of Type II and III C2 odontoid fractures, i.e., fractures at the base of the C2 odontoid or transversally to the body of the C2 vertebra; as well as Type III C2 traumatic spondylolisthesis, i.e., C2 "hangman fractures" with severe displacement and angulation. The Wertheim and Bohlman occipitocervical stabilization technique can be used for the treatment of fractures of the closed ring of the C1 vertebra, as well as for the stabilization of the C1-C2 segment when affected by rheumatoid arthritis.

Trauma, such as distractive flexion injuries with facet disruption and dislocation, or ligamentous injuries, to other cervical segments, for instance at the C5-C6 level or at the fulcrum between cervical and thoracic spine, can be treated using subaxial cervical stabilization with such wiring techniques as the Rogers technique, the Bohlman triple wire technique, the Dewar technique, or the Robinson and Southwick facet wiring technique.

Finally, among the thoraco-lumbar fractures that can be reduced and stabilised using wiring techniques, and in particular Harrington rods with sublaminar wires and interspinous wires, are compression fractures, flexion distraction fractures ("seatbelt fractures"), and dislocated fractures.

However, the metallic wires used in such wiring techniques present some drawbacks, in particular with respect to biocompatibility, strength, stability and material fatigue, and stress concentrations where they contact the bones. Even more significantly, adjusting the wire tension while tying the wire requires very high dexterity, and may be even more difficult once the wire is tied.

In the prior art, it has also been proposed to use flexible elongated elements other than wires to tie various implants to underlying osseous structures. In particular, intervertebral implants have been proposed which are tied to the vertebrae using flat bands, for instance in International Patent Application publication WO 2009/040380. Such flat bands have the advantages of higher biocompatibility, strength and stability, as well as better stress distribution on the bones. While adjusting the band tension remains difficult, this is less critical in this application, since the main stresses go through the body of the intervertebral implant, rather than the flat band.

SUMMARY

A first object of the disclosure is that of providing a device for securing a ligature to an osseous structure, wherein the tension in the ligature can be more easily adjusted than with previous devices and methods.

Accordingly, a device for securing a ligature to an osseous structure according to at least one illustrative embodiment of the disclosure comprises a first part, a second part, a flexible elongate member for engaging the osseous structure, the flexible elongated member being threaded through an orifice in the first part and a gap between the first and second parts, a closure element for clamping the first and second parts against each other so as to frictionally lock the flexible elongate member threaded through the gap between the first and second parts, and a deformable element between the first and the second part, which in an initial, undeformed position is suited to hold open said gap, and which in a second, deformed position allows the gap to be narrowed.

Because the deformable element holds the gap open in its undeformed position, the flexible elongate element remains free to slide through the gap, and the tension of the flexible elongate element can be easily adjusted without having to simultaneously hold the first and second parts apart from each other. The first and second parts can nevertheless be subsequently clamped against each other using the closure element, deforming the deformable element so that the gap is narrowed, and frictionally locking the flexible elongate member within this gap between the first and second parts.

The deformable element may be plastically or elastically deformable between said undeformed and deformed positions, wherein an elastically deformable element can provide an advantage of recovering its function of holding open the gap between the first and second parts if the closure element is subsequently released. On the other hand, a plastically deformable element may be more easily provided, and at a lower cost.

In some embodiments, the deformable element is solid with the first and/or the second part, reducing the number of separate parts of the device, thus simplifying both its production and operation and reducing the risk of incorrect assembly.

In some embodiments, the closure element is screwthreaded. In particular, said closure element may comprise a shank with an outer screw thread in engagement with a complementary inner screw thread in one of the first or second parts, and a head in engagement with the other one of the first or second parts. Consequently, the first part and the second part can easily be clamped against each other by tightening the closure element.

In some embodiments, the flexible elongate member has a first end and a second end, and each one of the first end and the second end is threaded through an orifice in the first part and a gap between the first and second parts. Consequently, both ends of the flexible elongate member can be simultaneously locked by closing the first part and the second part against each other.

Among some of these embodiments, each one of the first and second ends of the flexible elongate element is separately threaded through the gap. In particular, the first end of the flexible elongate element may be threaded through a first orifice in the first part, and the second end of the flexible elongated element may be threaded through a second orifice in the first part. The first and second ends of the flexible elongate element can thus be laterally offset with respect to each other, providing a more versatile ligature.

In some embodiments, the closure element is configured to releasably clamp the first and second parts against each other. The first and second parts could thus be released from each other after being clamped against each other, thus allowing a readjustment of the tension in the flexible elongate member.

In some embodiments, the flexible elongate member may comprise a flat band or a plurality of strands, in particular arranged side-by-side. Consequently, the stresses transmitted by the band or strands to the osseous structure are distributed over a wide area, preventing further damage to the bone structure.

Another object of the disclosure is that of providing an easier, safer method of securing a ligature to an osseous structure.

Accordingly, in at least an illustrative embodiment of the disclosure, a method for securing a ligature to an osseous structure comprises the steps of looping a flexible elongate member around at least part of the osseous structure, threading the flexible elongate member through a gap between the first part and the second part and an orifice of the first part, tensioning the flexible elongate member, so that the first and second parts are tightly bound to the osseous structure, and tightening a closure element between the first and second parts, so as to tighten the gap between the first and second parts against a resilience of a deformable element, and frictionally locking the flexible elongate element in the tightened gap between the first and second parts.

Because the resilience of the deformable element has to be overcome to tighten the gap and lock the flexible elongate member, the tension in said flexible elongate member remains easily adjustable until the closure element is actively operated, against the resilience of said deformable element, to clamp the first and second parts against each other.

In some embodiments, the flexible elongate member is threaded twice through the gap between the first part and the second part, so that both ends of the flexible elongate member can be frictionally locked by the tightening gap when the closure element is operated to close the first and second parts against each other.

In some embodiments, the osseous structure comprises a spine segment. In particular, it may comprise a cervical segment. The method according to the disclosure may be used, for instance, to treat Type II and III C2 odontoid fractures or Type III C2 traumatic spondylolisthesis with an upper cervical ligature according to the Gallie and Brooks atlanto-axial stabilization techniques. It may also be used for the treatment of fractures of the closed ring of the C1 vertebra, as well as for the stabilization of the C1-C2 segment when affected by rheumatoid arthritis, with an upper cervical ligature according to the Wertheim and Bohlman occipitocervical stabilization technique. Trauma to other cervical segments, such as distractive flexion injuries with facet disruption and dislocation, or ligamentous injuries, for instance at the C5-C6 level or at the fulcrum between cervical and thoracic spine, may be treated with a ligature to a corresponding spine segment following a known subaxial cervical stabilization technique. It must be understood that, although those techniques conventionally apply wires, according to the method a flat band or a plurality of strands may be tied to the osseous structure analogously to those wires, which has the additional advantage of distributing the contact stresses over wider areas of the bones.

The osseous structure may however also comprise a thoracic or lumbar segment. The method according to the disclosure may for instance be used to stabilize a thoracolumbar segment in case of a compression fracture, flexion distraction fracture, or dislocated fracture.

The method according to the disclosure may even be used to secure a ligature to other osseous structures than the spine, such as e.g. long bones, to secure implants and/or treat fractures. For instance, this method may be used for providing a rod-less arthrodesis, or for stabilizing a hip bone by trochanteric fixation using, for example, the Daii-Miles technique, or in hip revision surgery to prevent vessel necrosia or for a complementary rib ligature exerting a lateral rib traction for scoliosis correction.

The above summary of some example embodiments is not intended to describe each disclosed embodiment or every implementation of the invention. In particular, selected features of any illustrative embodiment within this specification may be incorporated into an additional embodiment unless clearly stated to the contrary.

BRIEF DESCRIPTION OF THE DRAWINGS

The disclosure may be more completely understood in consideration of the following detailed description of various embodiments in connection with the accompanying drawings, in which:

FIGS. 6A and 6B show detail cut views of the device of FIG. 1 through the same plane V-V, at successive stages of its operation to secure a ligature;

FIG. 7 shows a detail cut view of the device of FIG. 1 through plane IV-IV when the ligature is secured;

Figure 1:
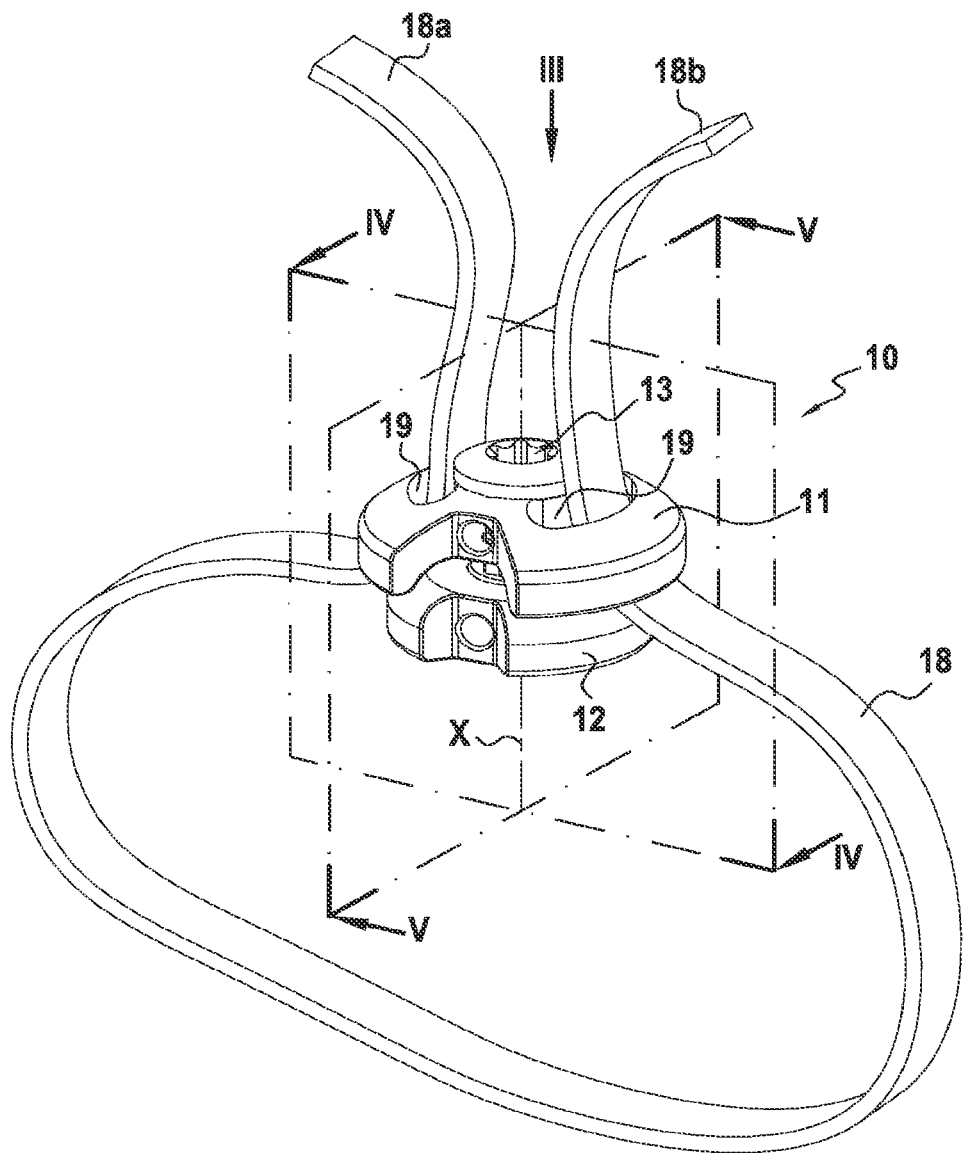
FIG. 1 is a perspective view of a device according to a first embodiment.

While the embodiments are amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the scope of the claims.

DETAILED DESCRIPTION

For the following defined terms, these definitions shall be applied, unless a different definition is given in the claims or elsewhere in this specification.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 2:
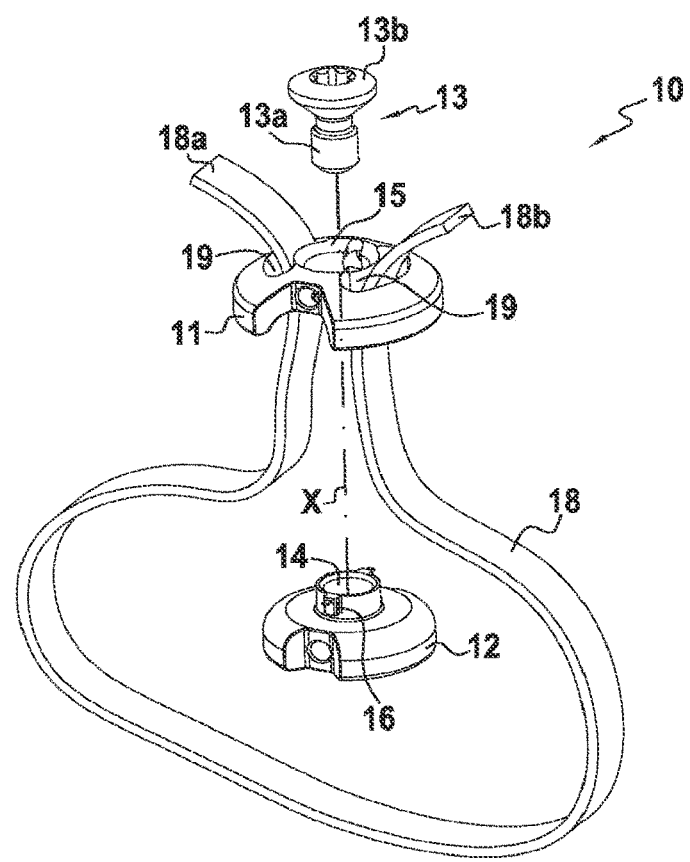
FIG. 2 is an exploded perspective view of the same device.

A device 10 for securing a ligature to an osseous structure according to a first embodiment is shown in FIGS. 1 and 2. In this particular embodiment, the device 10 is disc-shaped, which is an advantageous shape for its ease of handling and unobtrusiveness once implanted, but other alternative shapes may also be considered. This device 10 comprises a first part 11 and a second part 12 linked by a closure element 13 in the form of a screw with a screw-threaded shank 13a in engagement with a complementarily screw-threaded orifice 14 in the second part 12, and a head 13b in engagement with a recess 15 in the first part 11. Guiding blocks 16 protruding laterally from the second part 12 engage corresponding recesses 17 in the first part 11 to suppress rotation between the first and the second parts 11, 12, while still allowing their translation, relative to each other, along the longitudinal axis X of the screw 13.

The device 10 also comprises a flat, flexible band 18 adapted to form a ligature to an osseous structure. This band 18 is made of a biocompatible material, in particular comprising synthetic materials such as, but not limited to, polyester, polyethylene terephtalate (PET), ultra-high-molecular-weight polyethylene (UHMPE), or polyetheretherketone (PEEK).

Figure 8:
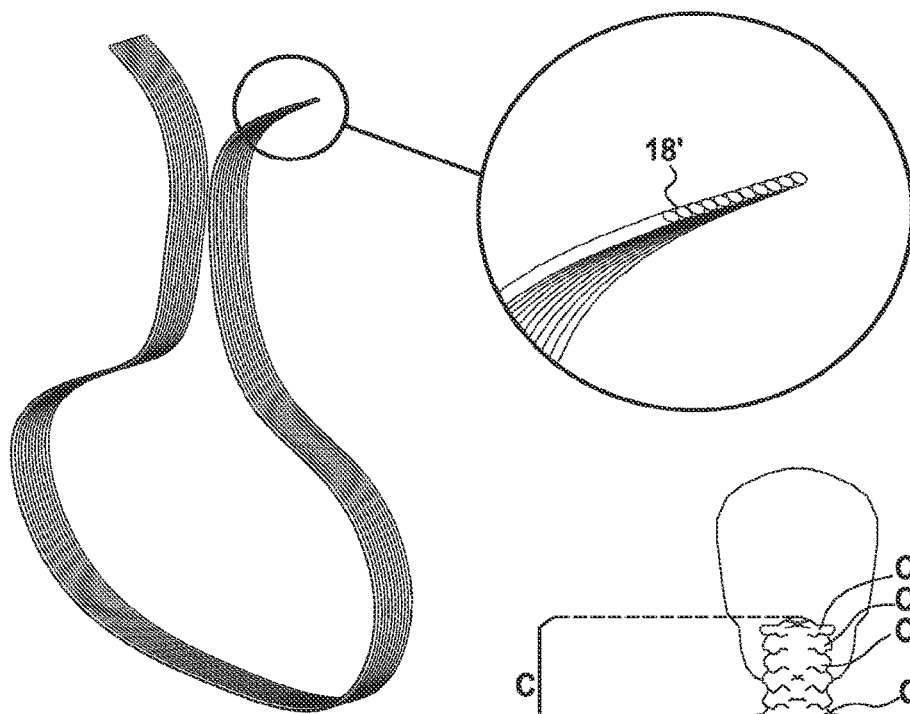
FIG. 8 shows a section of a flexible elongate element of a device according to a second embodiment.

While this first embodiment of the device 1 comprises a flat band 18, other types of flexible elongate members may alternatively be used for the ligature. For instance, in a second embodiment, a plurality of separate, substantially parallel strands 18', as illustrated in FIG. 8, could be used in place of the flat band of the first embodiment. The other parts of the device for securing this ligature to an osseous structure could be substantially equivalent to those of the first embodiment, and the device could be used analogously.

Figure 3:
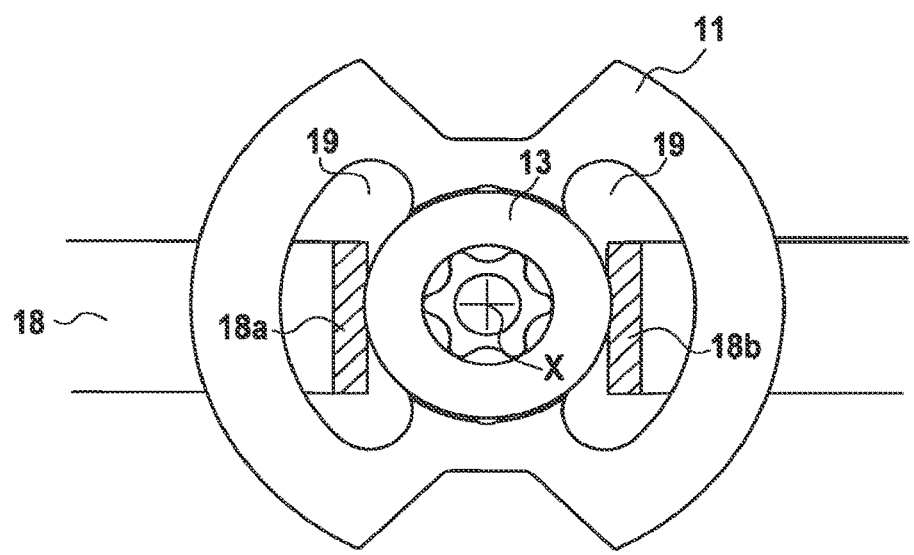
FIG. 3 is a top view of the device of FIG. 1.
Figure 4:
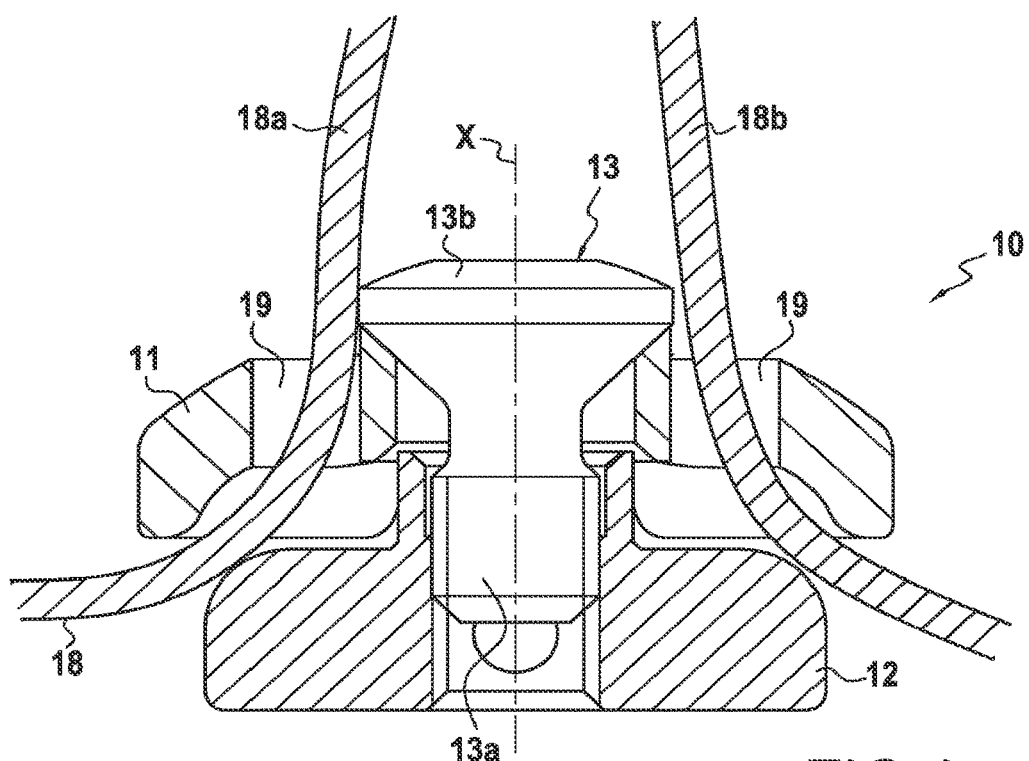
FIG. 4 is a cut view of the device of FIG. 1 through plane IV-IV.
Figure 5:
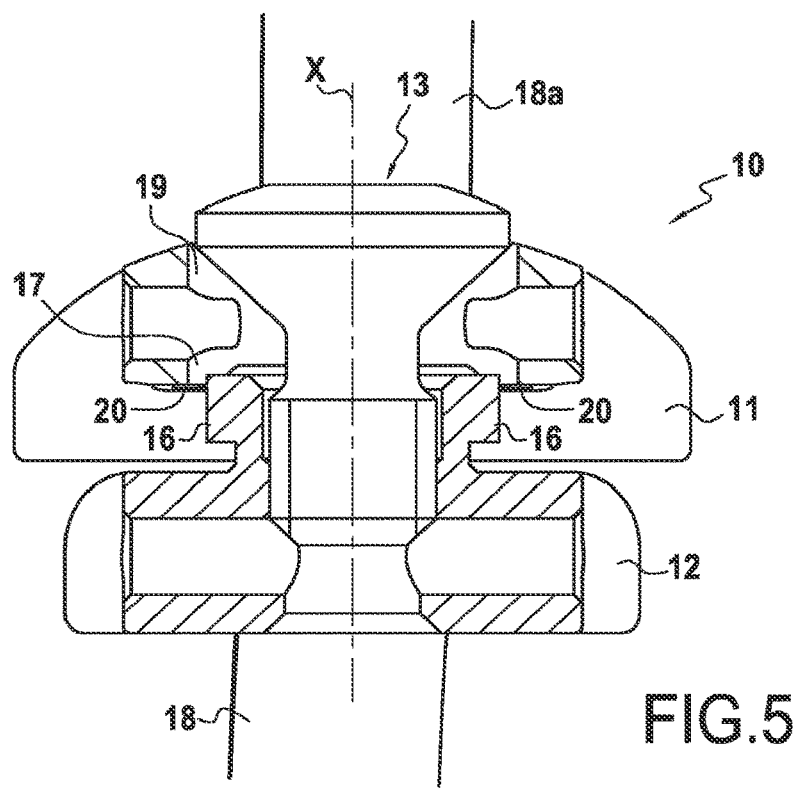
FIG. 5 is a cut view of the device of FIG. 1 through plane V-V.

Turning back to the first embodiment, each end 18a, 18b of the band 18 is threaded through one orifice 19 in the first part 11, and a gap G between the first part 11 and the second part 12, as can be seen in particular in FIGS. 3 and 4. As illustrated in FIG. 5, deformable, wing-shaped elements 20 protruding from each block 16 initially maintain this gap G, holding the bodies of the first and second part 11, 12 apart from each other.

In use, the width of the gap G initially maintained by the deformable elements 20 allows the band 18 to slid through the gap G and the orifices 19. Consequently, a user can easily make a ligature to an osseous structure using the band 18, and adjust the tension of the band 18 before securing this ligature. To secure the ligature the screw 13 is tightened in the orifice 14. Longitudinally guided by the blocks 16 in the recesses 17, the first and second parts 11, 12 will approach each other, progressively overcoming the resilience of the deformable elements 20 and bending them, as seen in FIGS. 6A and FIG. 6B, until arriving to a deformed position in which the gap G is so tightened that the first and second parts 11, 12 clamp around the band 18, as seen in FIG. 7, frictionally locking the band 18, and thus securing the ligature.

The screw 13 may be subsequently loosened again to readjust the band 18. If the deformable elements 20 have only been elastically deformed, they will return to their initial position illustrated in FIG. 5, holding the gap G open again. However, they will normally have been plastically deformed and will not return to their initial position. For a simple readjustment of the band 18, this will nevertheless not constitute a significant drawback for the user.

Figure 9:
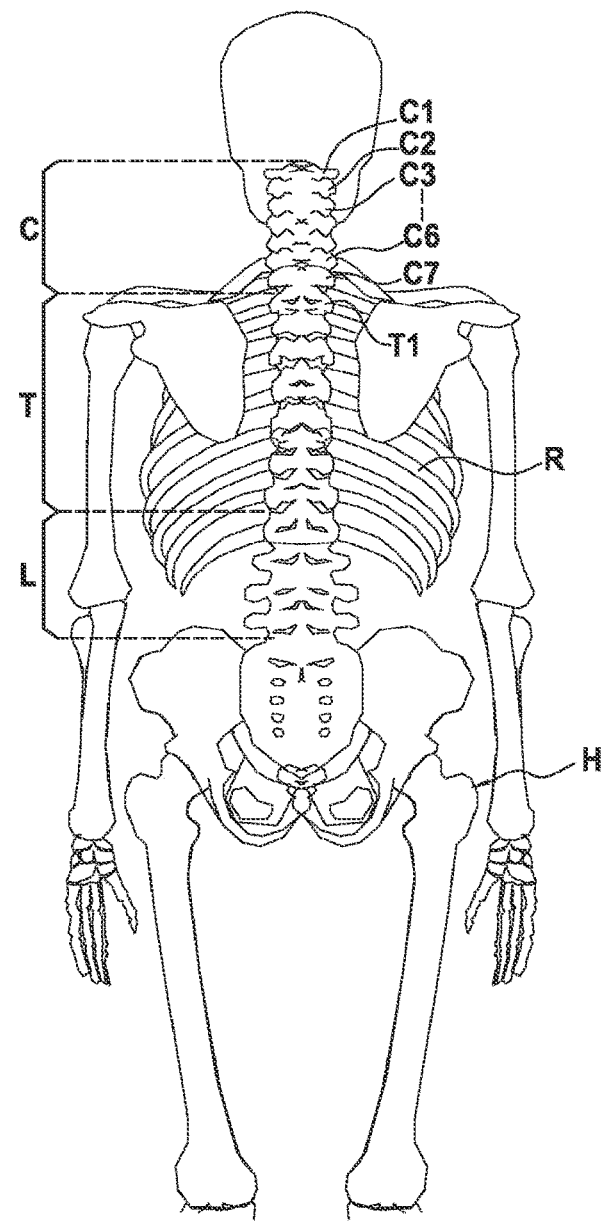
FIG. 9 shows a number of potential positions in a human skeleton for a ligature secured with the device of FIG. 1.

FIG. 9 illustrates several possible locations, in a human skeleton, for a ligature secured with the device 1. For instance, the ligature may be located in the upper cervical segment C1-C2 for the treatment of Type II and III C2 odontoid fractures, Type III C2 traumatic spondylolisthesis, fractures of the closed ring of the C1 vertebra, or for the stabilization of the C1-C2 segment when affected by rheumatoid arthritis. Such a ligature may also be used in the treatment of trauma to other cervical segments, such as distractive flexion injuries with facet disruption and dislocation, or ligamentous injuries, for instance at the C5-C6 level or at the fulcrum C7-T1 between cervical spine C and thoracic spineT, or to stabilise a segment of the thoracic spineT or lumbar spine L in case of a compression fracture, flexion distraction fracture, or dislocated fracture. The ligature may also might be applied also on other bony structures, such as e.g. long bones, to secure implants and/or treat fractures. It may, for instance, be used to stabilise a hipbone H, to exert a traction between ribs R, or to block any suitable joint by arthrodesis without rods.

Those skilled in the art will recognize that the invention may be manifested in a variety of forms other than the specific embodiments described and contemplated herein. Accordingly, departure in form and detail may be made without departing from the scope of the invention as described in the appended claims.

What is claimed:

1. A device for securing to an osseous structure, comprising:
   a first part including a first peripheral orifice, a second peripheral orifice, and a first central orifice extending along a longitudinal axis between the first peripheral orifice and the second peripheral orifice at a center of the device;
   a second part including a second central orifice at the center of the device;
   a ligature including a flexible elongate member for engaging the osseous structure, the flexible elongate member having a first end and a second end, wherein the flexible elongate member is positionable through both of the first and second peripheral orifices in the first part in a direction of the longitudinal axis and a gap between the first part and the second part;
   a threaded closure element extending through the first central orifice of the first part along the axis and engaging with the second central orifice of the second part, the threaded closure element configured to draw the first part and the second part together over a longitudinal distance along the longitudinal axis for clamping the first and second parts near each other so as to frictionally lock the flexible elongate member in the gap between the first and second parts; and
   a deformable element positioned between the first part and the second part and at least partially surrounding the closure element, wherein the deformable element is deflectable from an initial, undeformed position configured to hold open the gap, to a second, deformed position as the gap is narrowed upon tightening the threaded closure element.

2. The device for securing to an osseous structure according to claim 1, wherein the deformable element is plastically deformable.

3. The device for securing to an osseous structure according to claim 1, wherein the threaded closure element comprises a shank with an outer screw thread in engagement with a complementary inner screw thread in one of the first or second parts, and a head in engagement with the other one of the first or second parts.

4. The device for securing to an osseous structure according to claim 1, wherein the flexible elongate member, when positioned through the first peripheral orifice and through the second peripheral orifice, forms a loop.

5. The device for securing to an osseous structure according to claim 4, wherein each one of the first end and the second end of the flexible elongate member is separately positionable through the gap.

6. The device for securing to an osseous structure according to claim 1, wherein the threaded closure element is configured to releasably clamp the first part and the second part against each other.

7. The device for securing to an osseous structure according to claim 1, wherein the flexible elongate member comprises a flat band.

8. The device for securing to an osseous structure according to claim 7, wherein the flexible elongate member comprises a plurality of strands arranged in a single layer to form the flat band.

9. The device for securing to an osseous structure according to claim 1, further comprising:
a guide block positioned on one of the first part and the second part; and
a recess positioned on the other of the first part and the second part;
wherein the guide block slides in the recess to longitudinally guide the first part and the second part relative to each other.

10. The device for securing to an osseous structure according to claim 1, wherein the gap between the first part and the second part is formed by surfaces of the first part and the second part that cause the flexible elongate member to bend between the first part and the second part.

11. A device for securing to an osseous structure, comprising:
a first part including a first peripheral orifice, a second peripheral orifice, and a central orifice extending along a longitudinal axis, the first peripheral orifice and the second peripheral orifice extending through the first part in a direction parallel to the longitudinal axis;
a second part;
a ligature including a flexible elongate member for engaging the osseous structure, the flexible elongate member having a first end and a second end, wherein each of the first and second ends is threadable through one of the first and second peripheral orifices in the first part and through a gap between the first part and the second part, the gap extending transverse to the first peripheral orifice and the second peripheral orifice, and the ligature extends into the device at the first and second peripheral orifices in a direction parallel to the longitudinal axis and extends from the device at the gap in a direction transverse to the longitudinal axis;
a closure element passing through the central orifice of the first part and engaging with the second part for clamping the flexible elongate member between a surface of the first part and a surface of the second part that are transverse to the longitudinal axis so as to frictionally lock the flexible elongate member with respect to the first part and the second part and to cause the flexible elongate member to bend in a direction transverse to the longitudinal axis; and
a deformable element interacting with the first part and the second part, which in an initial, unlocked position is configured to hold apart the surface of the first part and the surface of the second part to permit the flexible elongate member to move between the surface of the first part and the surface of the second part, wherein upon actuation of the closure element to clamp the flexible elongate member between the surface of the first part and the surface of the second part, the deformable element is deformed to a second, deformed position in which the surface of the first part and the surface of the second part are closer together;
wherein the deformable element is deformable from the initial, unlocked position to the second, deformed position;
wherein the closure element threadably engages the second part to apply a clamping force to the flexible elongate member.

12. The device for securing to an osseous structure according to claim 11, wherein the first end of the flexible elongate member is threaded through the first peripheral orifice in the first part, and the second end of the flexible elongate member is threaded through the second peripheral orifice in the first part.

13. The device for securing to an osseous structure according to claim 11, wherein the deformable element is affixed to the first and/or the second part.

14. The device for securing to an osseous structure according to claim 11, wherein the closure element comprises a shank with an outer screw thread in engagement with a complementary inner screw thread in the second part, and a head in engagement with the first part.

15. The device for securing to an osseous structure according to claim 11, wherein the flexible elongate member comprises a flat band.

16. The device for securing to an osseous structure according to claim 11, wherein the flexible elongate member comprises a plurality of strands arranged in a single layer.

* * * * *